United States Patent
Co et al.

(10) Patent No.: US 6,228,024 B1
(45) Date of Patent: *May 8, 2001

(54) VASCULAR RETRACTOR

(75) Inventors: Fred H. Co, Santa Clara; Kevin H. Van Bladel, San Mateo, both of CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/299,693

(22) Filed: Apr. 26, 1999

Related U.S. Application Data

(63) Continuation of application No. 08/925,967, filed on Sep. 10, 1997, now Pat. No. 5,913,818, which is a continuation-in-part of application No. 08/867,133, filed on Jun. 2, 1997, now Pat. No. 6,033,361.

(51) Int. Cl.[7] ........................................ A61B 1/32
(52) U.S. Cl. .................... 600/204; 600/205; 600/210; 600/226; 600/231; 600/235
(58) Field of Search ..................... 600/204, 210, 600/201, 205, 206, 212, 215, 226, 227, 234, 235, 245, 231; 606/190

(56) References Cited

U.S. PATENT DOCUMENTS

| | | |
|---|---|---|
| 2,821,190 | 1/1958 | Chase ................................ 600/114 X |
| 4,232,660 * | 11/1980 | Coles . |
| 5,667,480 | 9/1997 | Knight et al. ......................... 600/210 |
| 5,722,934 * | 3/1998 | Knight et al. ..................... 600/210 X |
| 5,725,479 | 3/1998 | Knight et al. ......................... 600/210 |
| 5,759,150 | 6/1998 | Konou et al. ......................... 600/114 |
| 5,817,013 | 10/1998 | Ginn et al. ............................ 600/114 |
| 5,846,187 | 12/1998 | Wells et al. ........................... 600/201 |
| 5,846,191 | 12/1998 | Wells et al. ........................... 600/201 |
| 5,902,315 * | 5/1999 | DuBois ................................. 606/190 |
| 5,913,818 * | 6/1999 | Co et al. ............................... 600/204 |
| 5,922,004 * | 7/1999 | DuBois ................................. 606/190 |
| 6,033,361 * | 3/2000 | Co et al. ............................... 600/210 |

* cited by examiner

Primary Examiner—Jeffrey A. Smith

(57) ABSTRACT

A self-supporting retractor for holding open an anatomic space for performing endoscopic surgical procedures. The retractor includes a substantially rigid elongate member, having proximal and distal ends, and having an arch shape or "C" cross-section, defining a passage and longitudinal working window along the retractor. The distal end is preferably rounded or streamlined to facilitate insertion along a dissected space with minimized tissue trauma, and may include a hooded portion enclosing the passage at the distal end. The elongate member may include radially cooperating segments or self-retaining edges to maximize the area of the space held open by the retractor. The retractor may include a handle or a pivotable finger grip on the proximal end to manipulate the retractor during use, and/or a curved handle to tent the incision providing access to the dissected space. The retractor may also include a channel member for an endoscope, integrally formed or pivotally attached to the retractor.

32 Claims, 9 Drawing Sheets

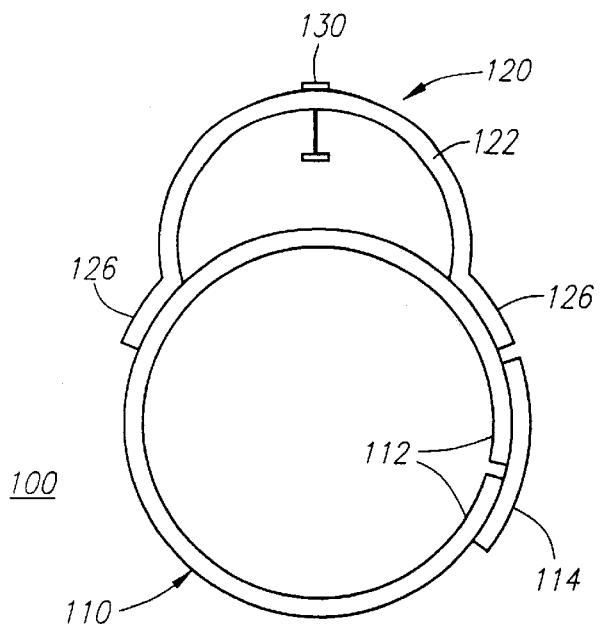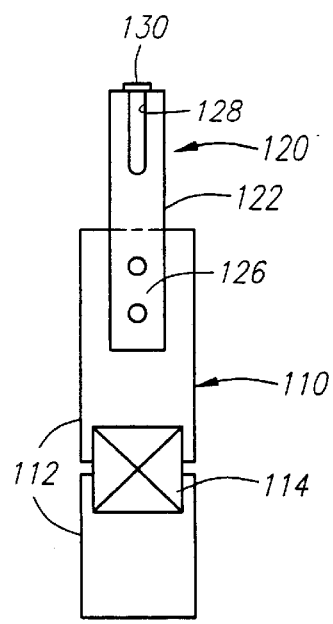
FIG. 12  FIG. 13
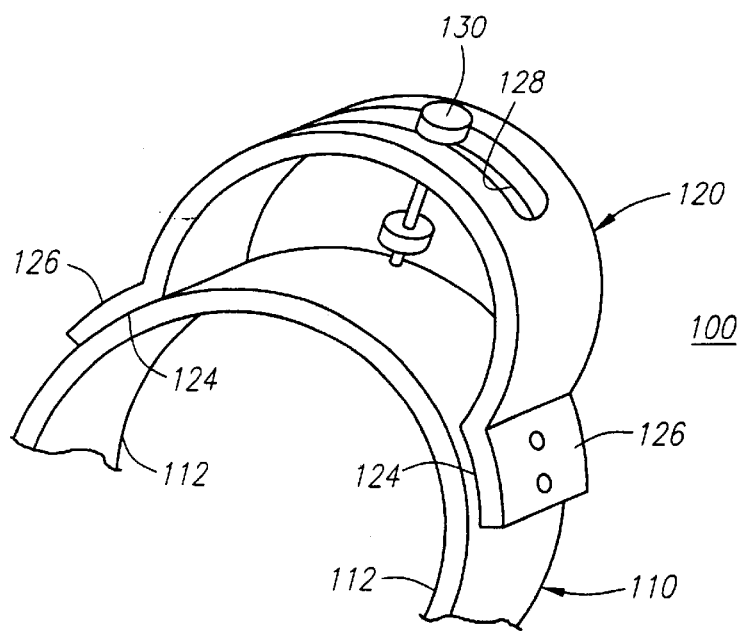
FIG. 14

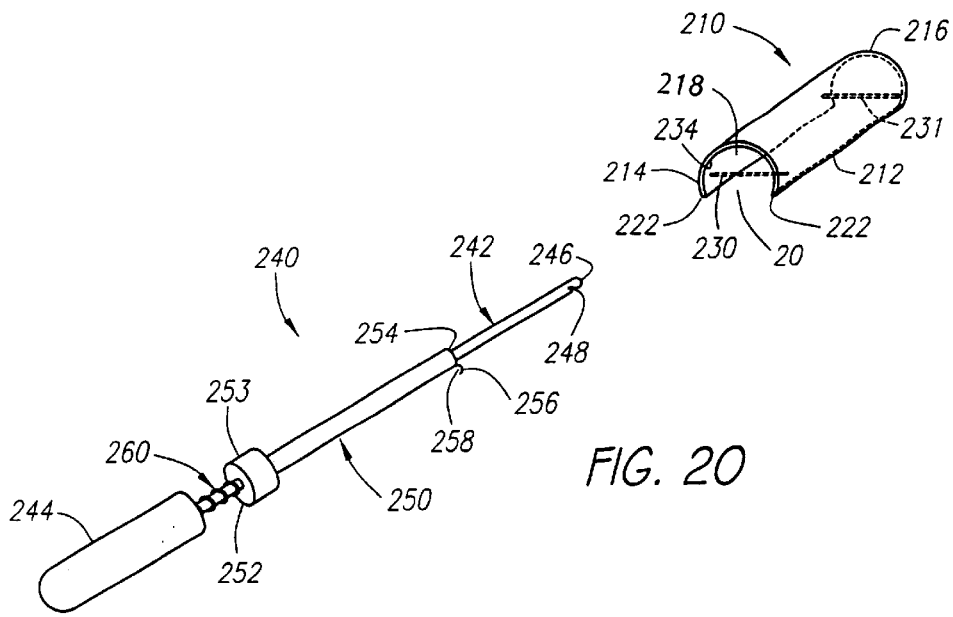
FIG. 20
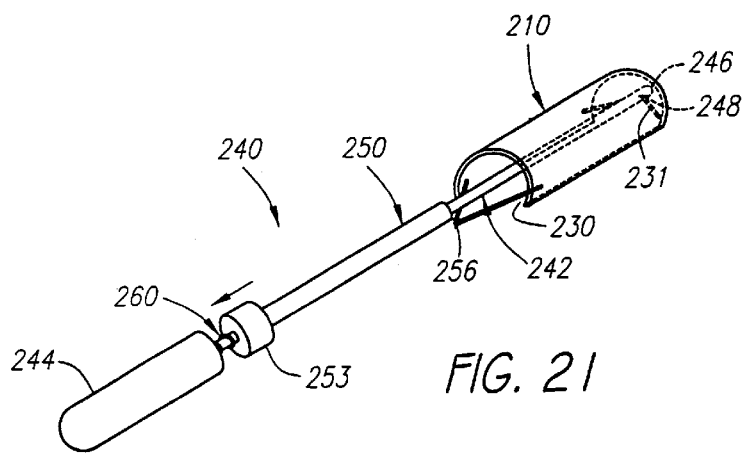
FIG. 21
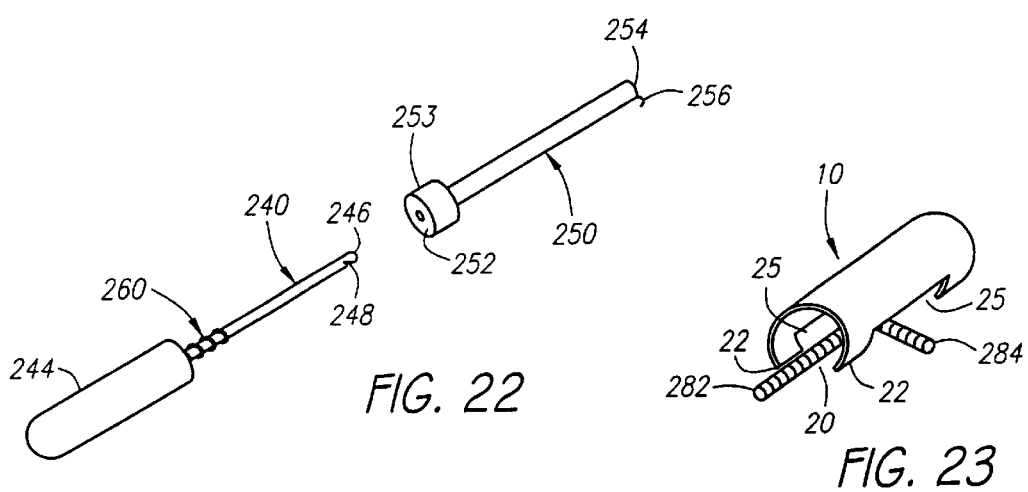
FIG. 22
FIG. 23

US 6,228,024 B1

VASCULAR RETRACTOR

This is a continuation of U.S. application Ser. No. 08/925,967, filed on Sep. 10, 1997, now U.S. Pat No. 5,913,818, which is a continuation-in-part of U.S. application Ser. No. 08/867,133, filed on Jun. 2, 1997, now U.S. Pat. No. 6,033,361. The priority of these prior applications is expressly claimed and their disclosures are hereby incorporated by reference in their entirety.

FIELD OF THE INVENTION

The present invention relates generally to surgical retractors, and more particularly to vascular retractors that are self-supporting and provide a longitudinal working window for endoscopic vascular harvesting procedures.

BACKGROUND OF THE INVENTION

Numerous surgical procedures have been developed to replace arteries that have become blocked by disease. For example, in coronary bypass surgery, a vein may be harvested from elsewhere in the body and grafted into place between the aorta and the coronary artery. It is generally preferred to use a vein taken from the patient undergoing the surgery, as the patient is a ready source of suitable veins that will not be rejected by the body after grafting. In particular, the saphenous vein in the leg is often used for this procedure. The saphenous vein is typically 3–mm in diameter, comparable in size to the coronary arteries. Furthermore, the venous system of the legs is sufficiently redundant that the saphenous vein may be removed and the remaining veins in the leg will continue to provide adequate return blood flow. Alternatively, the cephalic vein in the arm may sometimes be used as well.

Traditionally, to harvest the saphenous vein, an open surgical procedure has been used to expose and remove the vein from the leg. A series of incisions with skin bridges (and sometimes a long single incision) is made from the groin to the knee or to the ankle. Once the vein is exposed, the surgeon dissects the vein from the surrounding tissues, lifts the vein from the tissues, and divides and ligates the various tributary veins that feed into the saphenous vein. Once the vein is completely mobilized, the surgeon cuts the ends of the vein and removes it from the leg. The long incisions in the leg are closed, and the vein is prepared for implantation.

More recently, vein harvesting has been accomplished using endoscopic procedures. One or more small incisions are made at selected target sites for providing access to the vein being harvested. For example, to harvest the saphenous vein, an incision may be made at the groin, at the knee, and/or at the ankle. A tunneling instrument, such as a blunt or soft-tipped dissector may be utilized to dissect a subcutaneous space along the anterior surface of the vein being harvested. Such instruments generally include a substantially transparent elongate member having a rounded distal end and a passage therein for receiving an endoscope, the endoscope providing visualization through the end and/or side walls of the dissector. The tunneling instrument is inserted into the incision and advanced or pushed along between tissue layers to identify the saphenous vein. The tip of the dissector is generally kept in contact with the vein and the dissector is advanced along the tissues, thereby creating a small tunnel along the anterior surface of the vein. An inflatable balloon may then be introduced into the tunnel (or alternatively provided in a collapsed condition on the tunneling instrument prior to insertion into the incision), and inflated to enlarge and further propagate the tunnel. The balloon may be used to dissect fat and skin overlying the vein and to enlarge the tunnel to an appropriate size.

Once the desired length of vein is exposed and an appropriate tunnel developed, the balloon and/or dissector is removed, and a retractor, typically a wide flat shaft with a handle on its proximal end, is prepared. The retractor is inserted into the incision and directed along the dissected path over the section of vein to be harvested. The handle of the retractor may then be lifted away from the surface of the leg, creating a space under the shaft adjacent the vein.

Surgical instruments, such as a vein harvesting hook, may then be inserted into the space to strip away tissues surrounding the vein, ligate tributary veins, and mobilize the vein. Typically, the retractor has substantially transparent walls and an endoscope is provided in a passage in the retractor, thereby allowing visualization during the harvesting procedure.

Conventional retraction devices, such as those used in the vein harvesting procedure just described, often have limitations. For example, such retractors typically require external support to hold the retractor away from the surface of the vein and maintain the anatomic space. The surgeon may have to hold the handle on the retractor, preventing both hands from being free for the procedure or requiring an assistant. Alternatively, an external mechanical support may be provided to hold the retractor, but such a support may interfere with access to the operative site.

Some retractors include a distal hood capable of maintaining a space thereunder. These hoods, however, only create a limited self-supported space, requiring that the retractor be moved when it is desired to work in a new location. Such retractors also generally require external support to provide a space along the retractor shaft between the incision and the hooded space.

In addition, some retractors include a channel to direct an endoscope to the operative site. An endoscope inserted into such a conventional retractor, however, may not allow the surgeon to monitor the surgery as effectively as desired. For example, the walls of the retractor may cause glare or distortion impairing visualization of the vein. Further, although the endoscope may be moved axially within the channel in the retractor to view the section of vein, lateral movement may be limited without also moving the retractor itself. The proximal end of the endoscope may also partially obstruct the incision, and may impair introduction of surgical instruments into the anatomic space.

Accordingly, there is a need for a self-supporting retractor capable of holding open an anatomic space for endoscopic vascular procedures that does not require external support to maintain the space.

In addition, there is a need for a retractor for holding open an anatomic space for endoscopic procedures that provides improved visualization within the space.

SUMMARY OF THE INVENTION

The present invention is directed to a retractor for holding open an anatomic space for performing endoscopic surgical procedures. Generally, the retractor comprises a substantially rigid elongate member, having proximal and distal ends, and having a tunnel or an arcuate, arch shaped or "C" shaped cross-section to hold the dissected space open. The distal end is preferably rounded or streamlined to facilitate insertion along a dissected space with minimal tissue trauma. The cross-section of the elongate member defines a passage therein within the "C" extending distally from the proximal end, and provides a longitudinal working window along the passage between the longitudinal edges of the arch, that is, below the edges of the "C." The elongate member may be fabricated from any metal or plastic material suitable for surgical devices, but preferably is formed from a substantially transparent plastic, such as polycarbonate, to facilitate illumination and/or visualization within the space.

The elongate member may have a substantially uniform cross-section along its length, or it may be gradually tapered to suit particular applications where the anatomy of the patient requires large and small ends on the retractor. In addition, the elongate member may be a single formed piece, or it may include a plurality of cooperating segments. For example, the elongate member may include telescoping segments, allowing the length of the elongate member to be adjusted. Alternatively, the elongate member may include radially cooperating segments capable of being manipulated to increase or decrease the periphery of the arch, thereby adjusting the cross-sectional area of the anatomic space held open by the retractor.

The elongate member need not have a uniform cross-section along its entire length. The edges of the "C" cross-section may only extend to a maximum periphery intermittently such that elsewhere along the length of the elongate member there is a greater degree of tissue exposure, hence greater working access to tissue. Preferably, the section of maximum peripheral extension is near the distal end of the elongate member. If so constructed, the self-retaining effect is gained for a substantial length adjacent the section of maximum peripheral extension.

The retractor also may include a handle formed on or attached to the proximal end of the elongate member. A handle may be attached to the elongate member, for example substantially perpendicular to the longitudinal axis of the elongate member, to facilitate directing the retractor along the dissected space. In addition, the handle may include one or more finger grips pivotally attached to the proximal end of the elongate member to accommodate use with either the left or right hand of the surgeon performing the procedure.

In a further aspect, the handle may have an ergonomic design. The ergonomic handle is designed to fit comfortably in one hand of a surgeon and provide the surgeon greater control of the retractor during insertion, placement, and removal. The ergonomic handle is adapted to receive a scope and may further include a receptacle for holding a scope light in a near vertical direction.

Alternatively, a curved handle may be attached to or integrally formed on the proximal end, extending proximally therefrom and curving up and away from the passage defined by the elongate member. The handle may comprise an arch-shaped or curved proximal region that extends proximally from a straight distal region of the retractor. Such a curved handle or proximal region may hold open the incision accessing the dissected space, thereby facilitating insertion of the tools used to perform the intended procedure.

In addition, the retractor may also include a channel for an endoscope, a light source, or similar visualization apparatus. The channel need not extend the full length of the retractor, and may even be a ring. The endoscope channel may be integrally formed along an inside surface of the elongate member. For example, the endoscope channel may be defined by a "C"-shaped member integrally formed along the top of the arch and extending distally from the proximal end.

Alternatively, the endoscope channel may be pivotally attached to the elongate member. For example, a cylindrical sleeve, defining the endoscope channel therein, may be attached to the inside surface of the elongate member. The sleeve may include a tab extending therefrom that may be inserted into a similarly shaped hole or slot in the wall of the elongate member. The cooperating tab and hole frictionally engage one another, holding the sleeve in place. If the tab and hole are substantially round, they may also allow the sleeve, and consequently an endoscope inserted therein, to be pivoted about an axis defined by the tab and hole. Alternatively, the sleeve may be substantially permanently fixed to the elongate member, for example by force-fitting the tab into the hole, or by using suitable adhesives.

The retractor may also include an enclosed distal end or hooded portion. A hooded portion may be integrally formed on the distal end of the elongate member or a hood may be formed from a separate component attached to the elongate member. The hooded portion substantially encloses the distal end of the elongate member and includes a rounded distal surface, thereby facilitating insertion along a dissected space with minimal tissue trauma. The hooded portion may have a width comparable to the width of the elongate member, or may have a larger width to provide a wider anatomic space, and therefore a wider working window within the hooded portion. The hooded portion may also be substantially transparent, allowing illumination and/or visualization distally therethrough to monitor insertion of the retractor along the dissected space.

A retractor in accordance with the present invention may include other features as well. The retractor may include a light source built into the elongate member to provide illumination along the working window to aid in visualization. Alternatively, the proximal end may include a notched slot or other locking detents for holding a cable for a light source inserted into the passage. The proximal end may include a stand, such as a bipod, to help support the retractor and hold open the incision and/or the dissected space. The stand may be a concave-shaped balloon located at or near the proximal end or on the handle of the retractor. The inflatable stand is inflated upon insertion of the retractor into a portion of a patient's body. The inflatable stand rests on the patient thereby elevating and supporting the retractor. A proximal portion of the elongate member may include an elongate slot, for adjustably connecting the retractor to a support arch that may be attached to the patient adjacent the site of the incision.

Thus, it is an object of the present invention to provide an improved retractor for endoscopic procedures.

Additional objects and features of the present invention will become apparent from consideration of the following description taken in conjunction with the accompanying drawings.

BRIEF DESCRIPTION OF THE DRAWINGS

FIG. 12 is a perspective view of an adjustable support device for holding a retractor in accordance with the present invention.

FIG. 13 is an end view of the adjustable support device of FIG. 12.

FIG. 14 is a side view of the adjustable support device of FIG. 12.

FIG. 1 7 is a cross-sectional view of the retractor of FIG. 16 along line 17—17, showing the segments in a minimizing periphery position.

FIG. 20 is a perspective view of a preferred embodiment of a collapsible retractor and a tool for collapsing the retractor.

FIG. 21 is a perspective view of the tool of FIG. 20 holding the retractor in a collapsed condition.

FIG. 22 is a perspective view of a partially disassembled tool for collapsing a retractor.

FIG. 23 is a perspective view of a retractor in accordance with the present invention having extended notches for exposing a tributary vein.

DETAILED DESCRIPTION OF THE PREFERRED EMBODIMENTS

Figure 1:
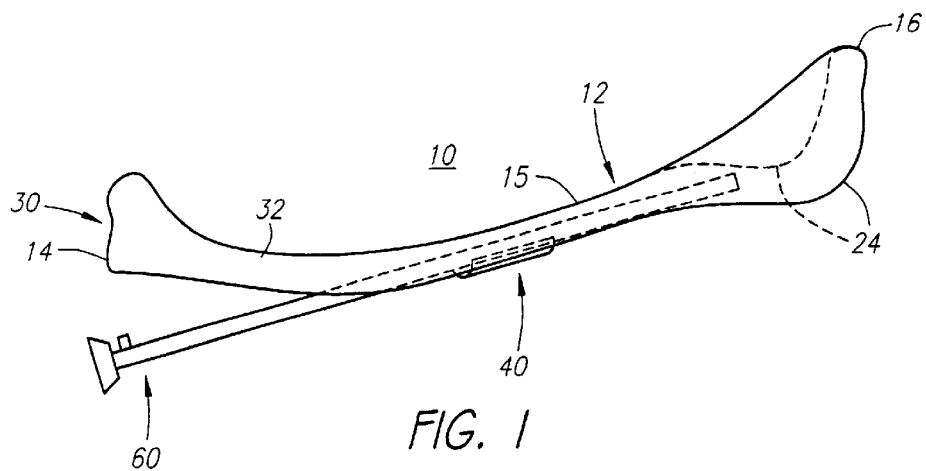
FIG. 1 is a perspective view of a first preferred embodiment of a vascular retractor in accordance with the present invention, with an endoscope received therein.
Figure 2:
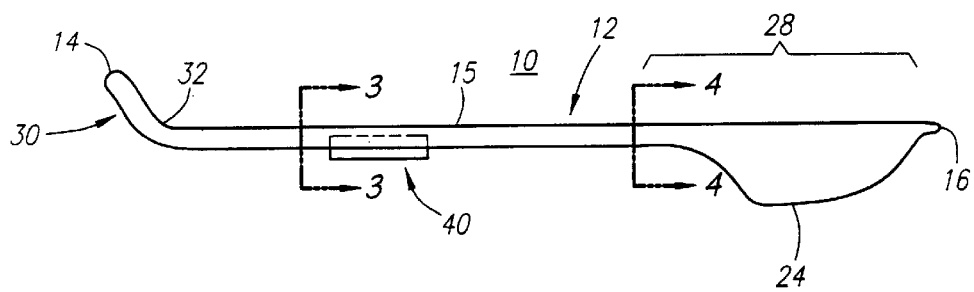
FIG. 2 is a side view of the vascular retractor of FIG. 1, without the endoscope.
Figure 3A:
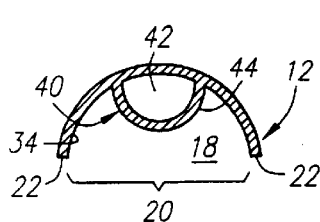
FIGS. 3A and 3B are cross-sections of the retractor of FIG. 2, taken along line 3—3, showing alternative embodiments of a channel for receiving an endoscope.
Figure 3B:
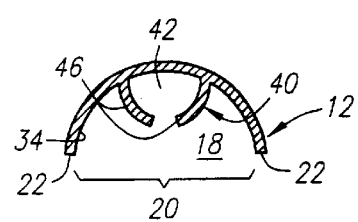

Turning now to the drawings, FIGS. 1 and 2 show a first preferred embodiment of a vascular retractor 10 in accordance with the present invention. The retractor 10 includes an elongate member 12, a handle 30, and an endoscope channel 40. The elongate member 12 has a proximal end 14, a distal end 16, and an arcuate or "C" cross-section, as shown in FIGS. 3A and 3B. The arcuate cross-section may define a portion of the periphery of a circle or an ellipse. The distal end 16 is preferably rounded or streamlined to minimize tissue trauma when the retractor 10 is directed along a dissected space in a patient (not shown). The elongate member 12 defines a passage 18 therein extending distally from the proximal end 14, and includes a longitudinal working window 20 along the passage 18 between the longitudinal edges 22 of the elongate member 12. The elongate member 12 may be fabricated from any suitable metal or plastic material, but preferably is formed from a substantially transparent plastic, such as polycarbonate. Alternatively, the elongate member may be formed from a flexible or resilient, semi-rigid material, such as extruded polyvinyl chloride (PVC).

Figure 4:
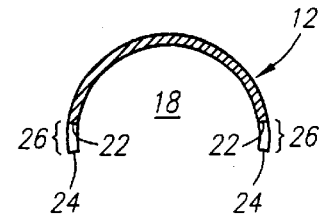
FIG. 4 is a cross-section of the retractor of FIG. 2, taken along line 4—4, showing circumferentially extended edges thereof.

The elongate member 12 includes circumferentially extended edges or curved tabs 24 integrally formed along a portion of the edges 22 of the elongate member 12 and extending peripherally from the edges 22, thereby defining an extended periphery 26, as shown in FIG. 4. The extended edges 24 increase the anatomic space held open by the retractor 10 since the extended periphery further tents the anatomic space, particularly at the location adjacent the extended edges 24. Although the extended edges 24 are shown located on a distal region 28 of the elongate member 12, alternatively they may be located at any predetermined location along the elongate member 12. Furthermore, one or more additional sets of extended edges (not shown) may be provided in other regions of the elongate member 12 to further support the anatomic space being held open.

The elongate member 12 also includes a curved proximal region or substantially rigid curved handle 30 integrally formed therein. The handle 30 extends proximally from a straight distal region 15 and curves up and away from the passage 18, the curved outer surface 32 being adapted to hold open or "tent" the incision (not shown) into which the retractor 10 is inserted, thereby facilitating introduction of surgical instruments for performing endoscopic procedures within the space held open by the retractor 10.

In addition, the retractor 10 also includes a channel member 40 for receiving an endoscope 60, having an arbitrary length extending along a portion of the elongate member 12. Alternatively, a light source or other visualization apparatus (not shown) having a diameter similar to an endoscope may be received by the channel member 40. As shown in FIGS. 3A and 3B, the channel member 40 is integrally formed along an inside surface 34 of the elongate member 12, thereby defining a channel 42 for receiving an endoscope (not shown in FIGS. 3A and 3B). FIG. 3A shows the channel member 40 as comprising a cylindrical sleeve 44 defining the channel 42, while FIG. 3B, shows a pair of curved elongate tabs 46 together forming a "C"-shape and defining the channel 42. Alternatively, as described below, a separate cylindrical sleeve or the like (not shown) may be pivotally attached to the elongate member 12 instead of the integral members shown.

Figure 24:
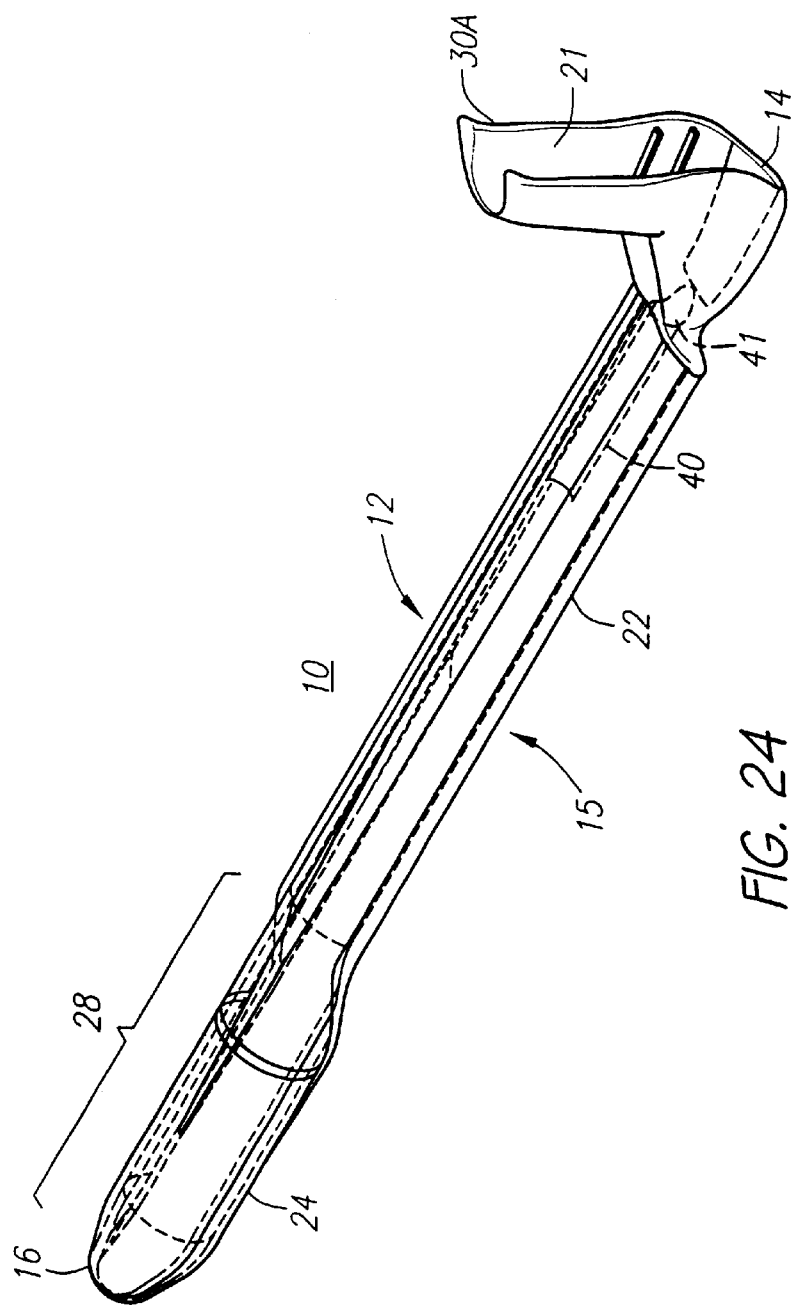
FIG. 24 is a perspective view of a retractor having an ergonomic handle in accordance with the present invention.

An alternative configuration of the first preferred embodiment is shown in FIG. 24. The retractor 10 of FIG. 24 is, in most respects, the same as the retractor 10 shown in FIGS. 1–4. Hence, throughout the description and figures, like reference numerals refer to like elements, and some elements are not explicitly described for all figures. The retractor 10 of FIG. 24 has an innovative ergonomic handle 30*a* attached to, or integral with, the proximal end of the elongate member 12.

The ergonomic handle 30*a* may be made of any suitable material, including the materials appropriate for the elongate member 12. The ergonomic handle 30*a* is shown in the preferred shape having a rounded distal side adapted to fit into the fingers of a hand gripping the handle 30*a*. This shape permits the surgeon to effectively grip the retractor 10 in one hand with enhanced maneuverability that affords precise motor control of the retractor 10 during insertion, placement, and removal into a body. The ergonomic handle 30a has an opening 41 through which a scope (not shown) or other visualization device may be inserted. The handle 30a further comprises a receptacle 21 adapted to receive and provide support for a scope light connector (not shown). The scope light connector may be secured by threads provided on the receptacle 21 or by any other suitable fastening method.

Figure 5:
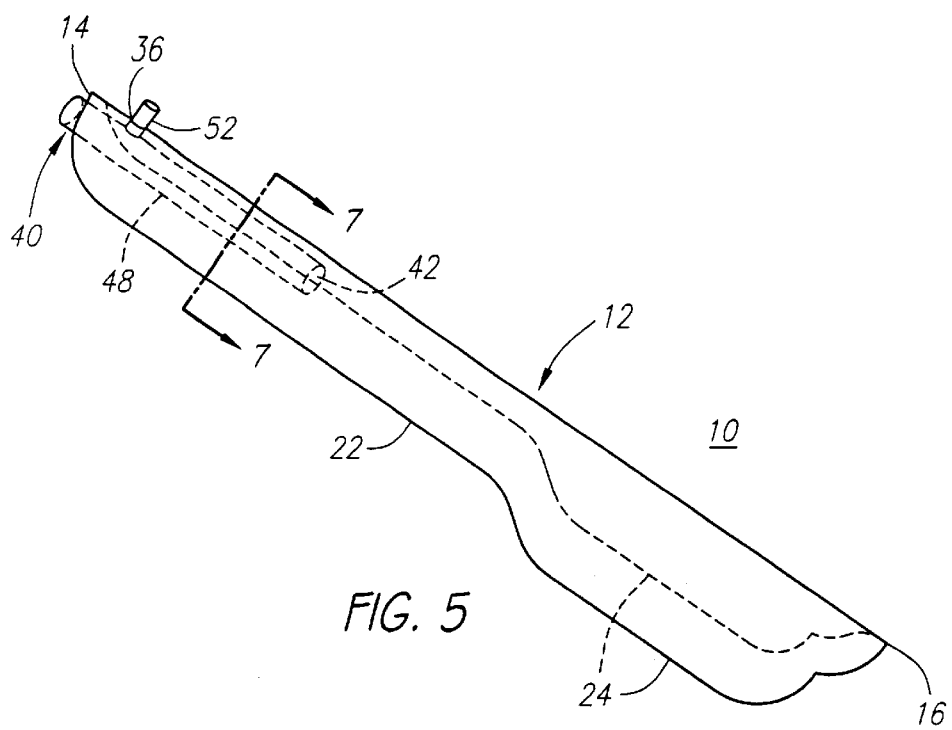
FIG. 5 is a perspective view of a second preferred embodiment of a retractor in accordance with the present invention, including a pivotable channel member for receiving an endoscope.
Figure 6:
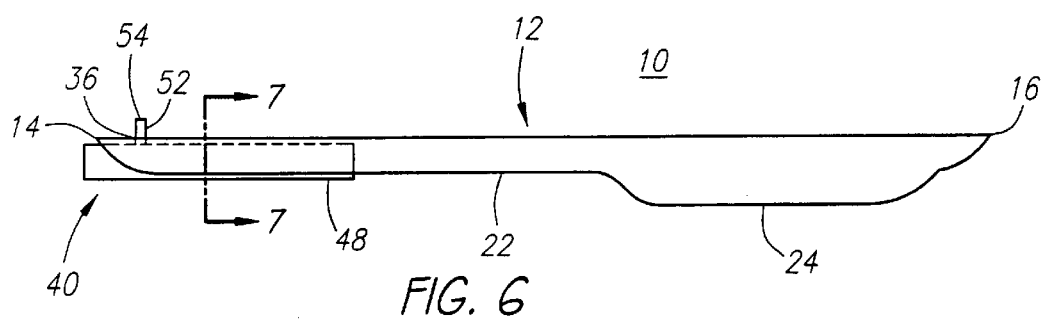
FIG. 6 is a side view of the retractor of FIG. 5.
Figure 7:
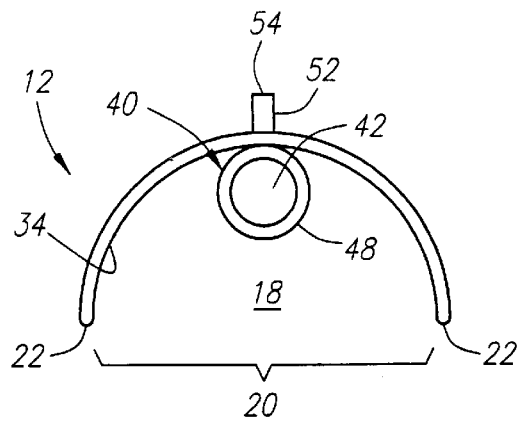
FIG. 7 is a cross-section of the retractor of FIG. 5, taken along line 7–7.

Turning now to FIGS. 5 and 6, a second preferred embodiment of a retractor 10 is shown. The retractor 10 includes a substantially rigid elongate member 12 and a channel member 40. The elongate member 12 has a proximal end 14 and a distal end 16, and has an arcuate or arch-shaped cross-section, as shown in FIG. 7. The proximal end 14 may be held to manipulate the retractor 10 and may be rounded to facilitate gripping the retractor 10, although optionally, a handle (not shown) may also be provided on the proximal end 14. The distal end 16 is preferably rounded or streamlined to minimize tissue trauma when the retractor 10 is directed along a dissected space in a patient (not shown). The elongate member 12 includes a passage 18 therein extending distally from the proximal end 14, defining a longitudinal working window 20 along the passage 18 between the longitudinal edges 22 of the elongate member 12. The elongate member 12 includes circumferentially extended edges 24 integrally formed along a portion of the edges 22 of the elongate member 12 and extending peripherally from the edges 22.

The retractor 10 also includes a channel member 40 for receiving an endoscope (not shown). The channel member 40 includes a cylindrical sleeve 48, defining a channel 42 for receiving an endoscope, which is attachable to an inside surface 34 of the elongate member 12 by a cylindrical tab 52 extending from the sleeve 48. The tab 52 is inserted into a similarly shaped hole 36 in the elongate member 12. The cooperating tab 52 and hole 36 frictionally engage one another, holding the sleeve 48 in place. Because the tab 52 and hole 36 are substantially round, the sleeve 48 may be pivoted about an axis 54. Consequently, an endoscope inserted into the sleeve 48 may also be pivoted laterally, thereby providing an increased field of view. Alternatively, the sleeve 48 may be substantially permanently fixed to the elongate member 12, for example by force-fitting the tab 52 into the hole 36, or by using suitable adhesives. In the case of substantially permanent attachment, the tab 52 and hole 36 may have a number of possible configurations that sufficiently cooperate, for example an elongate tab and slot (not shown).

Figure 8:
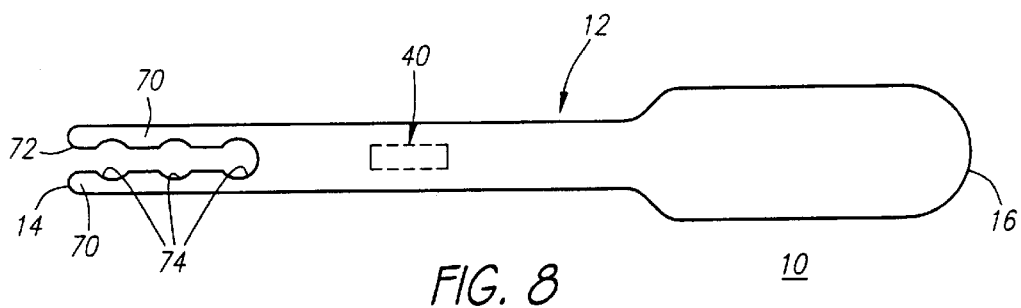
FIG. 8 is a top view of a retractor, including a locking mechanism for holding a light cable or like device.

In addition, as shown in FIG. 8, the retractor 10 may include locking detents 70 or other locking mechanisms, for example, on the proximal end 14, to hold a cable for a light or other instrument (not shown) that may be inserted into the anatomic space held open by the retractor 10. Preferably, the detents 70 are formed by an elongate slot 72 extending distally from the proximal end 14, and including a plurality of receiving regions 74 adapted to frictionally grip a cable inserted into the elongate slot 72. The detents may substantially fix the cable, minimizing obstruction within the anatomic space that could interfere with instruments inserted therein.

Figure 9:
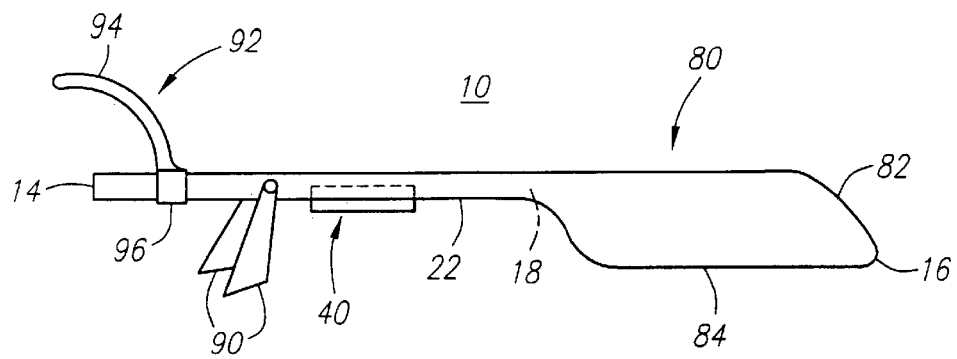
FIG. 9 is a side of view of another preferred embodiment of a retractor including a hooded portion and support legs.
Figure 10:
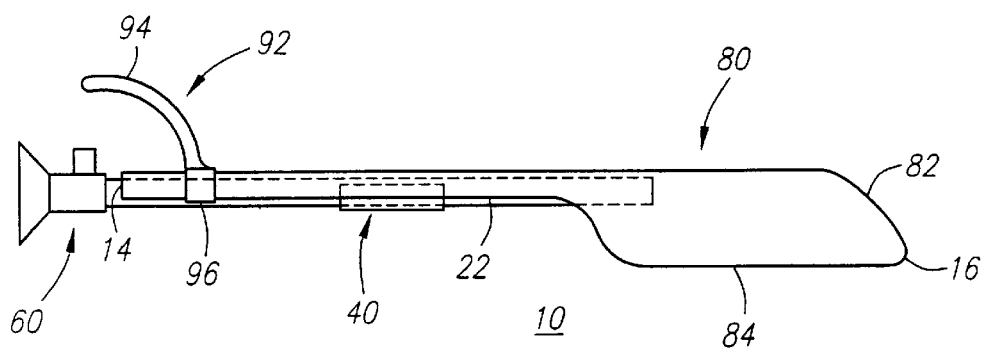
FIG. 10 is a side of a retractor with a hooded portion, and having an endoscope received therein.
Figure 11:
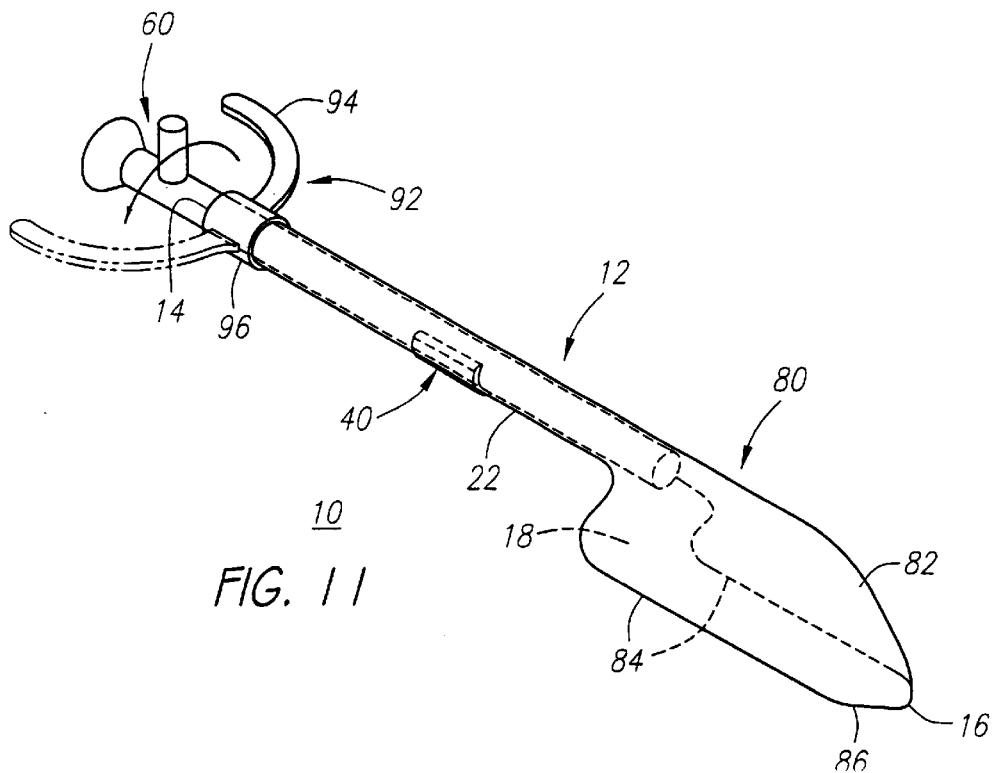
FIG. 11 is a perspective view of a retractor with a hooded portion, including a pivotable finger grip.
Figure 15:
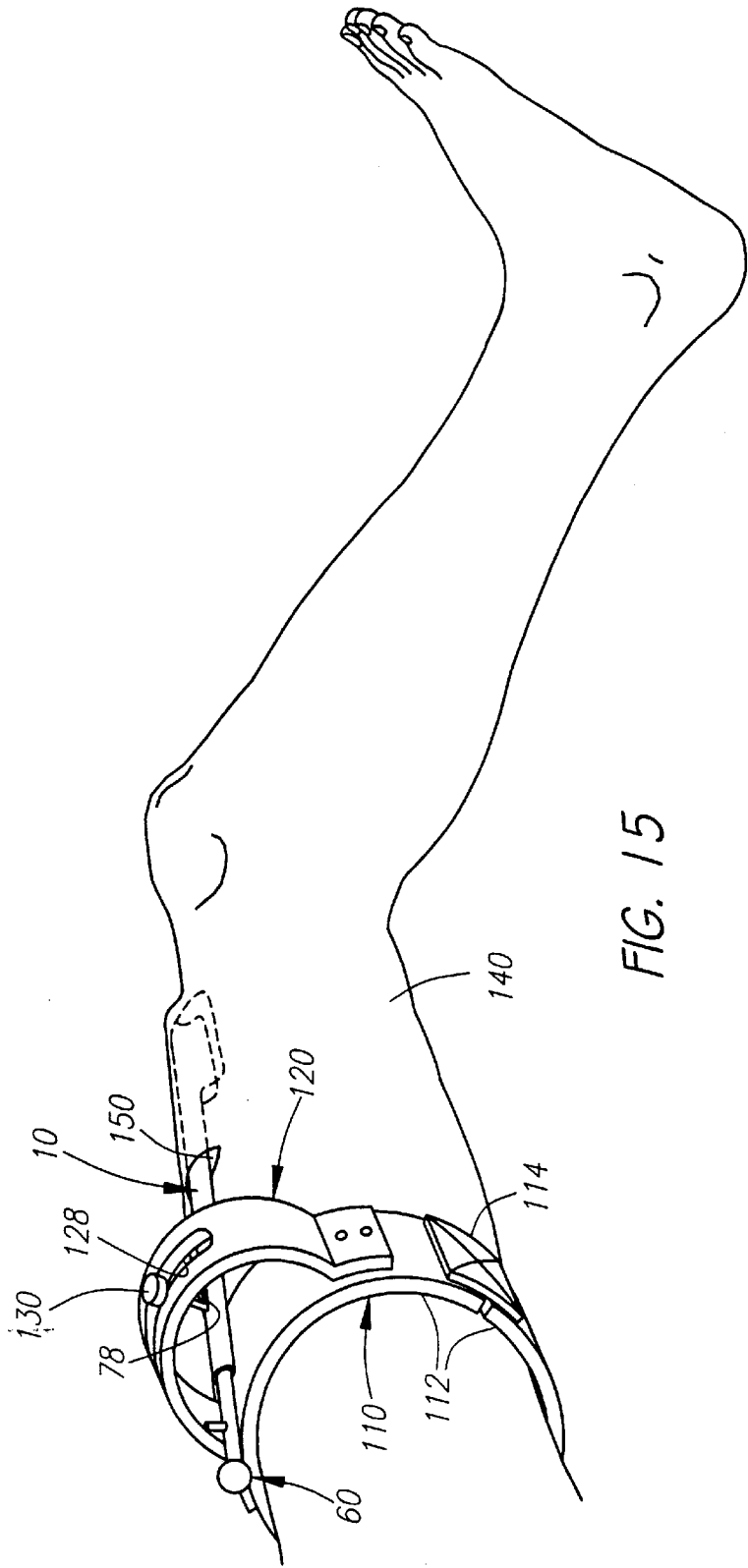
FIG. 15 is a perspective view of an adjustable support device strapped to a patient's leg and holding a retractor and endoscope inserted into an incision in the patient's leg.

Turning now to FIGS. 9–11, a third preferred embodiment of a retractor 10 in accordance with the present invention is shown. Similar to the previously described embodiments, the retractor 10 includes a substantially rigid elongate member 12 having a proximal end 14, a distal end 16, and an arcuate cross-section defining a passage 18. In this embodiment, the elongate member 12 also includes a hooded region 80 substantially enclosing the passage 18 at the distal end 16 of the elongate member 12. Preferably, the hooded region 80 is integrally formed on the elongate member 12, although alternatively, a separate hooded member (not shown) may be attached to the elongate member 12.

The hooded region 80 has a substantially rounded distal surface 82 to minimize tissue trauma when the retractor 10 is directed along a dissected space. In addition, the distal surface 82 is preferably substantially transparent, thereby allowing illumination and/or visualization through the distal surface 82 of the hooded region 80 of surrounding tissues when the retractor 10 is directed along the dissected space.

Figure 19:
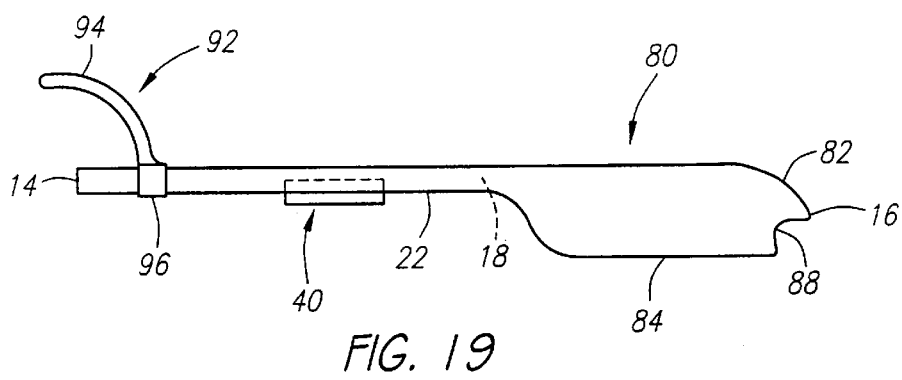
FIG. 19 is a cross-sectional view of a retractor with a hooded portion that includes a lateral tunnel on the distal tip.

The hooded region 80 also includes circumferentially extended edges 84 integrally formed along the longitudinal edges 22 of the elongate member 12 and extending peripherally from the edges 22, thereby defining an extended periphery to increase the anatomic space held open by the hooded region 80. The extended edges 84 may extend all along the edge 86 of the distal surface 82, thereby substantially enclosing the passage 18 at the distal end 16, or the edges 84 may be interrupted. For example, as in FIG. 19, a recessed region, such as the tunnel or notch 88, may be provided at the distal end 16 of the hooded region 80 to accommodate a blood vessel or other tissue structure (not shown). The tunnel 88 allows a structure therein to be accessed from within the hooded portion 80 without imposing an undesirable load directly onto the structure. The hooded region 80 may have a width comparable to the other portions of the elongate member 12, or may have a larger width to create a wider working window (not shown) covered by the hooded region 80.

The retractor 10 also includes a finger grip 92 to facilitate manipulation of the retractor 10 and/or the endoscope 60 received therein. Preferably, the finger grip 92 includes a substantially rigid curved handle 94 for being engaged by one or more fingers, although alternatively a ring or a straight handle (not shown) may also be provided. The handle 94 may be fixed to the proximal end 14 or, preferably, it may be pivotally attached thereto. For example, as shown in FIG. 11, the handle 94 may be mounted on a sleeve 96 that may rotate radially in relation to the elongate member 12, thereby allowing the finger grip 92 to accommodate both a left hand and a right hand. Alternatively, the elongate member 12 and finger grip 92 may include a cooperating slot and tab or other device (not shown) that allows rotation.

In addition, as shown in FIG. 9, the elongate member 12 may include additional support members or a stand, such as the legs 90 which together provide a bipod, for elevating the proximal end 14 of the retractor 10, for example at a predetermined height above the surface of a patient's leg. The legs 90 are preferably detachable from the elongate member 12, such as by snaps or tabs, allowing the legs 90 to be attached only when needed to tent the incision and facilitate the introduction of instruments into the passage 18.

Figure 25:
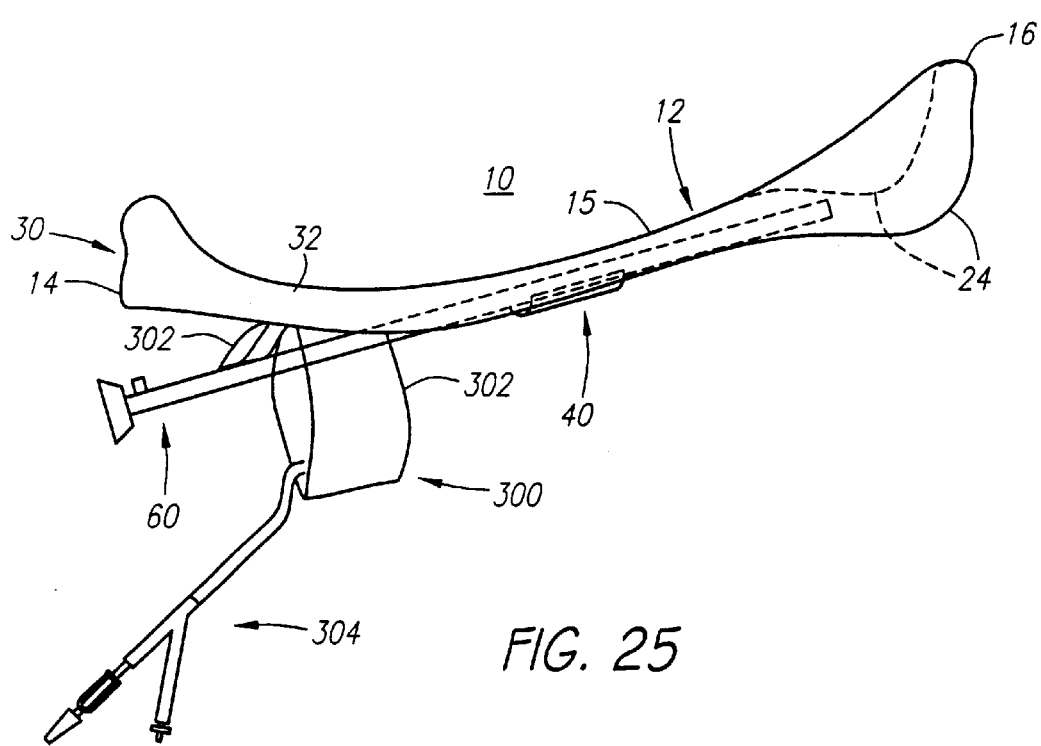
FIG. 25 is a perspective view of a retractor having an inflatable stand in accordance with the present invention.

Referring to FIG. 25, an alternative stand 300 for the retractor 10 is shown. The stand 300 comprises an inflatable balloon 302 attached to the proximal end 14 of the elongate member 22 or, alternatively, attached to the handle 32. The balloon 302 may include a single inflatable chamber having two portions in which each portion constitutes one leg of a bipod, or the balloon 302 may include two separate inflatable chambers, each comprising one leg of the bipod. The balloon 302 preferably forms a concave shape when inflated so that the stand 300 raises and supports the distal end of the retractor 10. The concave shape may be achieved by making the balloon 302 from a thin layer of sheet material attached to a thicker layer. When inflated, the thinner layer stretches more easily than the thick layer causing the balloon to become arched in a concave shape. The height of the stand 300 can be adjusted by controlling the inflation pressure.

An inflation harness 304 is connected to the balloon 302 for inflating the balloon 302. The inflation harness is of the same type as described in co-pending application Ser. No. 08/570,566, the disclosure of which is hereby incorporated by reference in its entirety.

The stand 300 is operated by inflating the balloon(s) 302 after the retractor 10 has been inserted and placed into a patient's body. The balloon(s) 302 form legs which can rest on the patient's body or any other appropriate support structure.

To facilitate use of a retractor in accordance with the present invention, an adjustable support device may be provided to hold open or tent the incision into which the retractor is inserted and adjust the orientation of the retractor. For example, FIGS. 12–15 show a support device 100 for use with a retractor 10 in accordance with the present invention. The support device 100 generally includes a fastening mechanism 110 for attaching the device, for example to a patient's leg 140 (FIG. 15), and a support arch 120. The fastening mechanism 110 includes a pair of straps 112 that may be wrapped around a leg, and a hook and eye (e.g. Velcro®) fastener 114 for securing the straps 112. Alternatively, the fastening mechanism 110 may include ties, notch and pin belts, adhesive tapes or similar mechanical fasteners (not shown) that may securely hold the support arch 120 in a fixed relationship to the site of the surgical procedure.

The support arch 120 is a substantially rigid arch member 122 attached to the fastening mechanism 110 at the base 124 of the arch member 122, for example by tabs 126 that may be stitched, glued, riveted or otherwise fastened to the straps 112. The arch member 122 includes an elongate slot 128 extending radially along the arch member 122. A connector 130, such as a threaded rod with locking nuts, is provided that may travel in the slot 128. The connector 130 may be fixed in a desired position along the slot 128 by loosening, adjusting, and tightening the connector 130. A retractor 10 (FIG. 15) may be attached to the connector 130, for example by an elongate slot 78, which allows the retractor 10 to be adjusted axially in relation to the incision 150 into which the retractor 10 is introduced.

The support device 100 may be provided from a variety of materials. For example, the straps 112 may be formed from fabric or flexible plastic tape. The support arch 120 may be made from substantially rigid materials, such as metal or engineered plastic, that provide sufficient support to hold a retractor attached thereto in a fixed position.

Thus, the retractor 10 may be inserted into the incision 150, and connected to the support device 100, for example, to hold the incision 150 open to facilitate introduction of surgical instruments therein. As desired during a procedure, the connector 130 may be loosened, allowing the retractor 10 to be adjusted proximally, distally, or laterally, and then may be fixed in a new position.

Figure 16:
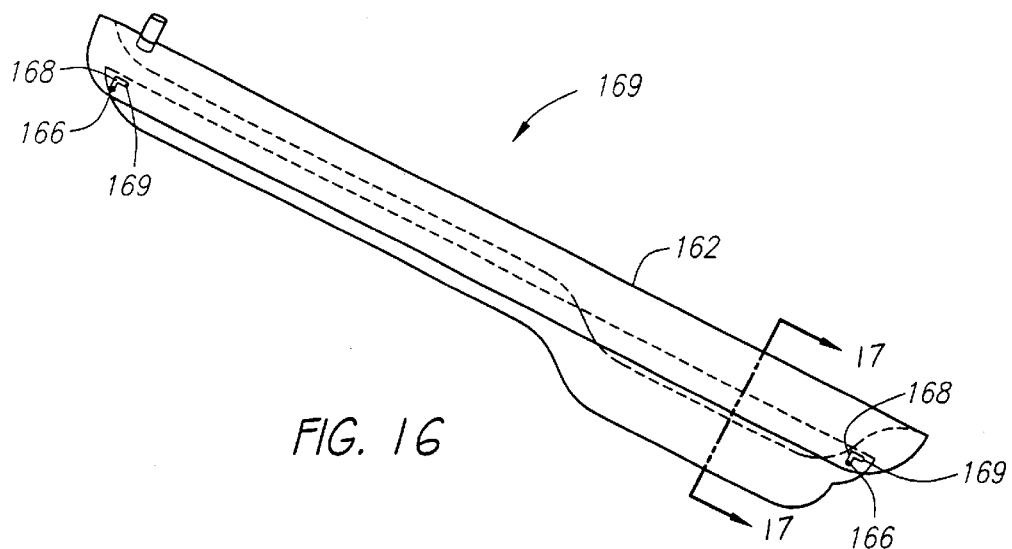
FIG. 16 is a perspective view of a retractor including two slidably cooperating segments.

In addition to the single piece elongate member as described in the previous embodiments, the retractor may include multiple cooperating elongate members. For example, as shown in FIG. 16, the retractor 160 may include two arcuate segments 162 and 164 that are slidably connected to one another, for example, by cooperating tabs 166 and slots 168. The first segment 162 includes one or more elongate slots 168, extending radially along the segment 162. The second segment 164 includes a tab or screw 166 that may be fixed in each slot 168, but able to slidably travel along the slot 168.

Figure 17:
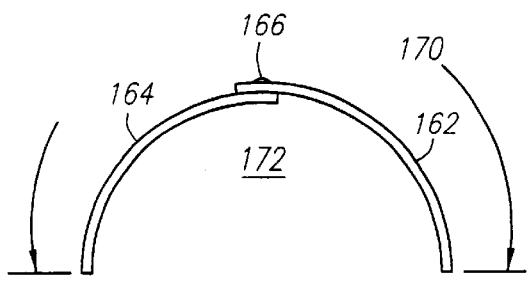
Figure 18:
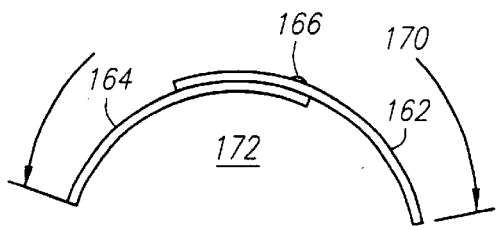
FIG. 18 is a cross-sectional view of the retractor of FIG. 16 along line 17—17, showing the segments in a maximizing periphery position.

As shown in FIGS. 17 and 18, the retractor 160 may be provided with the segments in a first relative position minimizing the periphery 170 defined by the segments 162, 164. Once the retractor 160 is fully inserted into a dissected space (not shown), the second segment 164 may be rotated to a position increasing the periphery 170 to maximize the cross-sectional area 172 held open by the retractor 160. The slots 168 may include a lateral locking region 169 into which the tabs 166 may be received to lock the segments 162, 164 in the periphery maximizing position. Alternatively, the elongate member may be provided from two or more segments with cooperating axial slots and tabs (not shown), thereby providing a retractor capable of telescoping distally and proximally as needed to provide an anatomic space of a particular length.

In another alternative embodiment, the retractor may be provided from a single piece of resilient, semi-rigid material, allowing the periphery to be minimized when the retractor is directed into and out of the anatomic space. For example, the longitudinal edges of the retractor may be rolled or compressed together, for example into a relatively small diameter cylinder, to facilitate the introduction of the retractor into a dissected space. Once in position, the elongate member may be released, and the edges may resiliently expand until the retractor assumes its arcuate or "C" shape, thereby holding the space open. Alternatively, only a distal most portion of the retractor may be furnished from a resilient, semi-rigid material, that may be compressed to facilitate introduction of the retractor, while the remaining portion may be formed from a substantially rigid material as previously described.

For example, FIGS. 20–22 show a preferred embodiment of a collapsible retractor 210 with an accompanying collapsing tool 240. The retractor 210 includes a tube or elongate member 212 having an arcuate or "C" shaped cross-section and fabricated from a substantially resilient, semi-rigid material, preferably biased to resume its "C" shape. For example, the tube 212 may be fabricated by extrusion from PVC material, possibly including an endoscope channel (not shown) simultaneously extruded and integrally formed along the inner surface 234 of the tube 212. The tube 212 may be extruded in its arcuate form, or a cylindrical tube (not shown) may be formed, with a lower portion of the periphery of the tube subsequently removed, such as by cutting longitudinally along the tube.

One or more flexible wires, strings or cables (shown, for example, as 230 and 231) may be attached to the tube 212 for collapsing the tube 212 to facilitate insertion of the retractor 210 into an anatomic space (not shown) and removal from the space. Preferably, a pair of wires 230 and 231 are attached across the passage 218 above the longitudinal edges 222 near the proximal end 214 and the distal end 216 of the tube 212 respectively. The wires 230, 231 may be fused or bonded to the inner surface 234 of the tube 212, or may extend through holes (not shown) where they may be knotted or otherwise fastened to the outside of the tube 212. The wires 230, 231 may be fabricated from any suitable inelastic but flexible material, such as stainless steel, nitinol or plastic. Thus, when the wires 230, 231 are tensioned, that is are directed axially towards or away from one another, the edges 222 are drawn together, thereby reducing the profile of the retractor 210.

To facilitate use of the collapsible aspect of the retractor 210, a collapsing tool 240 may be provided, preferably including only three parts, namely a shaft 242, a tube 250, and a spring 260. The parts may be fabricated from conventional materials, such as any suitable medical quality metal or plastic, that are sufficiently durable to allow the tool 240 to be disassembled after use for cleaning and reassembled for subsequent reuse. The shaft 242 preferably is a substantially rigid elongate member having a notch 248, or alternatively a hook (not shown), adjacent its distal end 246, and having a proximal handle 244. Preferably, the distal end 246 is rounded to minimize tissue trauma during use.

The spring 260 is a conventional helical spring or similar resiliently compressible device that may be received over the shaft 242. Alternatively, the tool 240 may be provided without the spring 260, although the spring 260 is preferred for biasing the tool 240 to release a retractor 210 held thereon, as explained below.

The tube 250 is a substantially rigid tubular member having a passage (not shown) extending longitudinally through it for slidably receiving the shaft 242 therein. The proximal end 252 includes an enlarged portion or grip 253 to facilitate holding the tube 250 and to abut the spring 260. The tube 250 also includes a hook 256 on its distal end 254 that points proximally, thereby defining a receiving region 258.

To assemble the collapsing tool 240 prior to use, the spring 260 is placed on the shaft 242, and the distal end 246 of the shaft 242 is inserted into the proximal end 252 of the passage in the tube 250 until the shaft 242 extends substantially beyond the distal end 254 of the tube 242. When the spring 260 is engaged, but not compressed, between the handle 244 and the grip 253, the tool 240 is in a first position for receiving a retractor 210 thereon (FIG. 20). The respective lengths of the shaft 242 and tube 250 are such that the resulting distance between the notch 248 and hook 256 corresponds substantially to the distance between the wires 230 and 231 on the retractor 210. Thus, when the distal end 246 of the tool 240 is directed into the passage 18 of the retractor 210, the wires 231 and 230 may be received respectively in the notch 248 and the hook 256.

The grip 253 may then be pulled proximally towards the handle 244, compressing the spring 260, and increasing the distance between the notch 248 and the hook 256. As the wires 230 and 231 are pulled away from each other, the resulting tension draws the edges 222 of the retractor 210 together, thereby reducing the profile of the retractor 210 (FIG. 21). The resulting collapsed condition of the retractor 210 thus facilitates insertion and removal of the retractor 210.

Once the retractor 210 is delivered to a desired location within a dissected space, the collapsed retractor 210 is deployed by releasing the grip 253. As the spring 260 directs the hook 254 distally, the wires are released, allowing the retractor 210 to resiliently resume its "C" shape and consequently hold the anatomic space substantially open. The tool 240 may then be withdrawn from the space, and the desired endoscopic procedure performed. Upon completion of the procedure, the retractor 210 may be removed by reinserting the tool 240 into the space until it receives the wires 230 and 231 once again, whereupon the grip 253 may be drawn proximally, drawing the wires and collapsing the retractor 210 for removal.

In an alternative embodiment, the retractor 210 may be fabricated from a semi-rigid wire mesh, such as a material similar to those used for coronary stents. The retractor 210 would then be capable of maintaining a collapsed condition, having a reduced profile for facilitating insertion, and an expanded condition such as the "C" shape described above, for holding an anatomic space open. The tool 240 may also include an inflatable balloon (not shown) on the shaft 242, and the retractor 210 may be placed on the shaft 242 over the balloon. The retractor 210 may be held on the shaft 242 by the wires 230, 231 received within the notch 248 and hook 256 on the tool as described above. Alternatively, the retractor 210 may be provided without wires, and the notch 248 and hook 254 may engage the wire mesh of the retractor 210 directly. The distal end 246 of the tool with the retractor 210 thereon may be inserted into a dissected space to a desired location. The retractor 210 may then be deployed, for example, by releasing the retractor 210 and inflating the balloon, thereby expanding the retractor 210 to its expanded condition. The tool may be removed until completion of the procedure within the space, whereupon the tool may be inserted into the passage 18 to remove the retractor 210. The notch 248 and hook 252 may engage the wires or the wire mesh directly to collapse the retractor 210 for removal.

In a further alternative embodiment, the retractor 210 may be provided from a substantially rigid material, such as polycarbonate, eliminating the need for the wires 230 and 231. Instead of using the tool 240 to collapse the retractor 210, the tool 240 may be used to facilitate insertion and removal of the retractor 210 within a dissected space. For example, the retractor 210 may include elongate openings (not shown) adjacent the proximal and distal ends 214, 216 for receiving the notch 248 and the hook 254. Alternatively, the notch 248 and the hook 254 may be oriented towards one another (not shown), thereby allowing the tool 240 to directly grab the ends 214, 216 of the retractor 210. The notch 248 and hook 254 may be inserted into the openings, and the grip 253 may be pulled proximally, increasing the distance between the notch 248 and the hook, and thereby gripping the retractor 210. Alternatively, if the ends 214, 216 are gripped directly, the grip 253 may be pulled, the retractor 210 placed between the notch 248 and the hook 254, and the grip 253 released, allowing the notch 248 and the hook 254 to engage the distal and proximal ends 216, 214 respectively, thereby substantially grabbing the retractor 210. The distal end 246 of the tool 240 with the retractor 210 thereon may be inserted into an anatomic space, the retractor 210 may be released, and the tool 240 removed. After the procedure is completed, the tool 240 may be introduced into the passage 18, and the retractor 210 may be gripped again for removal.

Alternative configurations for the tool described herein may also be provided, if they allow the notch and hook (or alternatively, a first and second hook) to be slid distally and proximally in relation to one another. For example, a notch or hook may be placed on the end of a rail and a hook may then be slidably mounted on the rail, such as on a substantially rigid shaft that has a length smaller than the length of the rail. In addition, the tool may include a locking mechanism or detents, such as a detachable hook or a cooperating tab and slot, to hold the notch and hook in a predetermined position, for example in the hold or release positions.

To facilitate performance of an endoscopic procedure, optionally, any of the embodiments of the retractor described herein may also include a built-in light source (not shown) to illuminate the passage 18 and/or the working window 20 to enhance visualization. In addition, as shown in FIG. 23, a retractor 10 may include one or more notches 25 extending up from the longitudinal edges 22 of the retractor 10. For example the notches 25 may extend along a region of the retractor 10 to better expose side branches extending laterally from the working window 20, such as a tributary vein 284 that may feed into a vein 282 being harvested, as shown.

A principal feature of a retractor in accordance with the present invention is providing a self-supporting device capable of holding open an anatomic space for endoscopic surgery. Conventional methods may be used to create an incision and dissect an anatomic space, for example for endoscopic vein harvesting in a patient's leg. For example, U.S. Pat. No. 5,601,581, issued to Fogarty et al., discloses an apparatus and method suitable for dissecting an anatomic space. The disclosure of this reference and any others cited herein are expressly incorporated herein by reference. To summarize, a section of a tissue structure, for example a nerve or vein, especially the saphenous vein, is selected to be harvested. An incision is created at a location adjacent to one end of the selected structure, such as at the groin or knee. A tunneling instrument, such as a blunt or soft-tipped dissector including an inflatable balloon thereon, is inserted into the incision and advanced along between tissue layers to identify the selected structure, and then is advanced along the anterior surface of the structure to create a small tunnel. The balloon is inflated to enlarge the tunnel and may be used to dissect fat and skin overlying the structure to develop a tunnel of a desired size. The balloon is then deflated, and the tunneling instrument is removed from the dissected space.

A retractor in accordance with the present invention may then be inserted into the incision and directed along the dissected space while orienting the longitudinal working window towards the structure . An endoscope may be inserted into the passage and retained by the channel member of the retractor, thereby allowing visualization of the space and along the working window. The arcuate shape of the described embodiments allow the tissues anterior to the surgical site, such as the tissues anterior to the saphenous vein, to be held up and away from the site without needing external support. The longitudinal edges of the arcuate retractor abut the subcutaneous tissues adjacent the anterior surface of the selected structure, the longitudinal working window defined by the edges providing access along a desired length, for example of the vein being harvested. Surgical instruments may be introduced into the incision and directed along the passage defined by the retractor to any point along the length of the working window without having to relocate the retractor, for example to perform an endoscopic vein harvesting procedure. If a pivotable channel member is provided on the retractor, the endoscope may be pivoted, as well as being directed axially, to observe the procedure being performed within the space. Thus, a retractor in accordance with the present invention may allow a vein, nerve or similar elongate tissue structure to be harvested without having to relocate the retractor during the procedure.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A retractor for holding open an anatomic space developed in a patient for performing an endoscopic procedure therein, said retractor comprising:

a substantially rigid elongate member having proximal and distal ends, said elongate member having a generally arcuate cross-section defining a passage therein extending between said proximal and distal ends;

an endoscope channel, said channel being on an inside surface of said elongate member and extending distally along a portion thereof; and an ergonomic handle located at said proximal end of said elongate member.

2. The retractor of claim 1 wherein said endoscope channel is integrally formed along said inside surface of said elongate member.

3. The retractor of claim 2 wherein said endoscope channel comprises a "C"-shaped channel defining a passage therein for slidably receiving an endoscope.

4. The retractor of claim 1 wherein said endoscope channel comprises a hollow cylindrical sleeve pivotally attached to said inside surface of said elongate member.

5. The retractor of claim 1 wherein said distal end includes a substantially rounded distal end to facilitate insertion of said retractor into a dissected space in a patient.

6. The retractor of claim 1 wherein a distal region of said elongate member includes a hood enclosing said passage at said distal end.

7. The retractor of claim 6 wherein said hood is substantially transparent, thereby allowing visualization of tissues through said hood when said retractor is directed along a dissected space in a patient.

8. The retractor of claim 6 wherein said hood is substantially transparent, thereby allowing illumination of tissues through said hood when said retractor is directed along a dissected space in a patient.

9. The retractor of claim 1 wherein said elongate member includes a finger grip attached to said proximal end for facilitating directing said elongate member during insertion into an anatomic space.

10. The retractor of claim 9 wherein said finger grip is rotationally attached to said proximal end, thereby facilitating gripping of said proximal end with either hand.

11. The retractor of claim 1 wherein said ergonomic handle further comprises a receptacle adapted to receive a scope light.

12. The retractor of claim 1 wherein said elongate member has a tapered cross-section between said proximal and distal ends.

13. The retractor of claim 1 wherein said retractor comprises substantially transparent plastic.

14. The retractor of claim 1 further comprising an inflatable stand on said proximal end of said elongate member wherein inflation of said stand elevates and supports said retractor.

15. The retractor of claim 1 further comprising detents for detachably holding a cable from an instrument introduced into said passage.

16. The retractor of claim 15 wherein said detents comprise a notched slot on said proximal end.

17. The retractor of claim 1 wherein said elongate member is provided with circumferentially extended edges.

18. The retractor of claim 17 wherein said extended edges are in a distal region of said elongate member.

19. The retractor of claim 18 comprising additional extended edges in a region of said elongate member proximate to said extended edges in said distal region.

20. The retractor of claim 17 wherein said extended edges comprise tabs integrally formed in said elongate member.

21. The retractor of claim 1 wherein a distal region of said elongate member is provided with circumferentially extended edges, thereby providing an enlarged cross-section of said passage.

22. The retractor of claim 21 wherein said extended edges comprise tabs integrally formed in said elongate member, thereby defining an extended periphery.

23. The retractor of claim 21 comprising additional extended edges in a portion of said elongate member proximate to said extended edges in said distal region.

24. The retractor of claim 21 wherein said elongate member includes a finger grip attached to said proximal end for facilitating directing said elongate member during insertion into an anatomic space, said finger grip being rotatable about a longitudinal axis of said elongate member, thereby facilitating use by either hand.

25. The retractor of claim 21 wherein said distal region includes a hood enclosing said passage at said distal end.

26. The retractor of claim 1 further comprising:

a substantially rigid arcuate segment slidably attached to said elongate member, said arcuate segment having an arcuate cross-section;

wherein said arcuate segment may slide rotationally in relation to said elongate member between first and second positions; thereby decreasing or increasing a periphery of said retractor.

27. The retractor of claim 26 wherein said elongate member and arcuate segment include a cooperating slot and tab for slidably attaching said arcuate segment to said elongate member.

28. The retractor of claim 1 wherein said elongate member has a curved proximal region, said curved proximal region extending proximally from a straight distal region and curving away from said passage, thereby facilitating insertion of instruments into an incision tented by said proximal region.

29. The retractor of claim 28 wherein said endoscope channel is pivotally attached to said inside surface of said elongate member, and extending distally along a portion of said passage.

30. The retractor of claim 1 wherein said endoscope channel is pivotally attached to said inside surface of said elongate member.

31. The retractor of claim 1 further comprising:

an inflatable balloon attachable to the retractor; and an inflation device for inflating said balloon.

32. The support device of claim 31 wherein said balloon is shaped to form a plurality of legs when inflated.

\* \* \* \* \*